US012153000B2

(12) United States Patent
Herth et al.

(10) Patent No.: US 12,153,000 B2
(45) Date of Patent: Nov. 26, 2024

(54) MICROSTRIP-TYPE MICROWAVE SENSOR

(71) Applicants: UNIVERSITÉ PARIS-SACLAY, Orsay (FR); CENTRE NATIONAL DE LA RECHERCHE SCIENTIFIQUE, Paris (FR); UNIVERSITÉ DE LILLE, Lille (FR); ASSOCIATION YNCRÉA HAUTS-DE-FRANCE, Lille (FR); ECOLE CENTRALE DE LILLE, Villeneuve-d'Ascq (FR); UNIVERSITÉ POLYTECHNIQUE HAUTS-DE-FRANCE, Valenciennes (FR)

(72) Inventors: Etienne Herth, Villeneuve Saint Georges (FR); Christophe Loyez, Festubert (FR); Laurie Calvet, Versailles (FR)

(73) Assignees: UNIVERSITÉ PARIS-SACLAY, Gif sur Yvette (FR); CENTRE NATIONAL DE LA RECHERCHE SCIENTIFIQUE, Paris (FR); UNIVERSITÉ DE LILLE, Lille (FR); ASSOCIATION YNCREA HAUTS-DE-FRANCE, Lille (FR); ECOLE CENTRALE DE LILLE, Villeneuve-d'Ascq (FR); UNIVERSITÉ POLYTECHNIQUE HAUTS-DE-FRANCE, Valenciennes (FR)

( * ) Notice: Subject to any disclaimer, the term of this patent is extended or adjusted under 35 U.S.C. 154(b) by 548 days.

(21) Appl. No.: 17/413,857

(22) PCT Filed: Dec. 11, 2019

(86) PCT No.: PCT/EP2019/084698
§ 371 (c)(1),
(2) Date: Jun. 14, 2021

(87) PCT Pub. No.: WO2020/120598
PCT Pub. Date: Jun. 18, 2020

(65) Prior Publication Data
US 2022/0042926 A1    Feb. 10, 2022

(30) Foreign Application Priority Data

Dec. 14, 2018  (FR) ........................ 1872939

(51) Int. Cl.
*G01N 22/00*    (2006.01)
(52) U.S. Cl.
CPC ................................ *G01N 22/00* (2013.01)
(58) Field of Classification Search
CPC ...................................................... G01N 22/00
See application file for complete search history.

(56) References Cited

U.S. PATENT DOCUMENTS 5,128,621 A  *  7/1992  Berthaud ............... G01N 22/00
                                                        324/636
5,334,941 A     8/1994  King
(Continued)

FOREIGN PATENT DOCUMENTS

CN    107490727 A    12/2017
CN    107655902 A    2/2018

OTHER PUBLICATIONS

Muhammad Amin et al., Slow Wave Applications of Electromagnetically Induced Transparency in Microstrip Resonater, Scientific Reports, www.nature.com/scientificreports <http://www.nature.com/scientificreports, pp. 1-13, Feb. 5, 2018.

Primary Examiner — Marcus E Windrich
(74) Attorney, Agent, or Firm — Oliff PLC

(57) ABSTRACT

A microstrip-type microwave sensor for the measurement of the dielectric properties of a solid or liquid material, con-
(Continued)

stituted by a main line and two connected transmission lines integral at one of their extremities to the main line, the main line and two connected transmission lines being spaced from one another by a slot and being made integral with a substrate. The main line is connected to an electrical circuit by each of its two extremities to inject a sinusoidal signal, and wherein said main line has a width giving it an impedance in the range 50 Ohm, the two connected transmission lines being of the same width and of a length equal to one quarter of the wavelength guided in the substrate, the substrate having a height or thickness giving it flexibility or rigidity, the substrate being applied to a metallic support formed of a layer of metallic material.

11 Claims, 10 Drawing Sheets

(56) References Cited

U.S. PATENT DOCUMENTS

| | | | |
|---|---|---|---|
| 6,441,622 B1 * | 8/2002 | Wrzesinski | H01Q 1/04 343/788 |
| 6,617,861 B1 | 9/2003 | Joshi | |
| 2005/0156784 A1 * | 7/2005 | Ryken | H01Q 9/0442 343/770 |
| 2011/0019259 A1 * | 1/2011 | Yen | G02F 1/0126 359/240 |
| 2013/0302843 A1 | 11/2013 | Son et al. | |
| 2014/0347073 A1 * | 11/2014 | Brown | G01R 31/311 324/637 |
| 2016/0025655 A1 * | 1/2016 | Blick | G01N 33/48721 324/637 |
| 2017/0179594 A1 * | 6/2017 | Liao | H01Q 1/246 |
| 2017/0350830 A1 * | 12/2017 | Karimi | G01N 33/2823 |
| 2018/0219531 A1 * | 8/2018 | Ramzan | H01P 7/082 |
| 2023/0211300 A1 * | 7/2023 | Herth | B01F 33/3021 366/111 |
| 2023/0344145 A1 * | 10/2023 | Zhang | H01Q 21/28 |

* cited by examiner

MICROSTRIP-TYPE MICROWAVE SENSOR

SCOPE OF THE INVENTION

The technical scope of the present invention is that of submersible microwave sensors in the form of a microstrip able to characterize and consequently detect the dielectric properties of a solid or liquid material.

STATE OF THE ART

Numerous studies have been undertaken to characterize the properties of a material by microwave frequencies using interferometric methods. These studies focus on the measurement of the dielectric constant and dielectric losses at different frequency ranges.

Thus, the article published by Muhammad Amin, Rashad Ramzan and Omar Siddiqui in the review SCIENTIFIC REPORTS, Vol. 8, 23357, dated May 2, 2018 and titled "Slow Wave Applications of Electromagnetically Induced Transparency in Microstrip Resonator" describes the use of a microstrip as the equivalent of a designated RLC resonator. It indicates that a microstrip may be used as a capacitor, inductor or resonant circuit. This document essentially focuses on the resonance of a single, double or triple microstrip in a frequency range from 1 to 2 GHz. No application is envisaged to characterize a liquid or solid material.

Reference may also be made to document US-2013/0302843 describing a biomaterial detector using a sensitive unit arranged in a channel on which two electrodes are applied, the biomaterials being placed between the two electrodes. No microstrips are proposed or suggested in this document.

Document CN-107490727 describes a hyperfrequency sensor incorporating two microstrip lines. This document is not specific about the structure of the microstrip lines and it states that the sensor thus designed has a higher sensitivity and greater accuracy in the measurement of the dielectric constant.

Document CN-107655902 describes a process to measure the concentration of a solution using a circular sensor with hyper frequency resonant cavity.

Reference may also be made to U.S. Pat. No. 6,617,861 which generally discusses a set of devices (line, microstrip ring or patch, coplanar line and stripline) and a method to measure the permittivity of solid or liquid materials. This document essentially discusses transmission measurements (two ports) or reflection measurements (one port) of a solid affixed to the sensor in a frequency range from 0.5 to 20 GHz. No clear indication is made to characterize materials in liquid state or for materials of small size.

DESCRIPTION OF THE INVENTION

The aim of the present invention is to propose a microwave sensor, submersible or not, enabling the nature of a liquid or solid material to be detected by defining a resonant microwave structure according to the dielectric properties of said material.

The invention thus relates to a microstrip-type microwave sensor for the measurement of the dielectric properties of a solid or liquid material, constituted by a main line and at least two connected transmission lines integral at one of their extremities with the main line, the main line and the at least two connected transmission lines being spaced from one another by a slot and being made integral with a substrate, wherein the main line is connected to an electrical circuit by each of its two respective extremities to inject a sinusoidal signal, and wherein said main line has a width giving it an impedance in the range of 50 Ohm, the at least two connected transmission lines being substantially of the same width and of a length equal to at least one quarter of the wavelength guided in the substrate, the substrate having a height or thickness (h) giving it flexibility or rigidity, the substrate being applied to a metallic support formed of a layer of metallic material.

According to one characteristic of the microwave sensor according to the invention, the assembly formed by the substrate and the lines is electrically insulated by means of an insulating coating formed of a thin layer of a polymer.

Advantageously, the insulating coating is formed of parylene with a thickness in the range of 1 to 40 µm.

According to another characteristic of the microwave sensor according to the invention, the slot has a width in the range of 100 µm to 5 mm.

According to yet another characteristic of the microwave sensor according to the invention, the metallic layer has a thickness in the range of 35 µm.

According to another characteristic of the microwave sensor according to the invention, the height (h) of the substrate is of between 500 and 1500 µm and is advantageously in the range of 800 µm.

According to yet another characteristic of the microwave sensor according to the invention, the substrate has a permittivity of between 1 and 40, and advantageously in the range of 2.55.

According to yet another characteristic of the microwave sensor according to the invention, the slot delimited by the at least two connected transmission lines constitutes reception means for said solid or liquid material.

According to yet another characteristic of the microwave sensor according to the invention, it incorporates at least two connected transmission lines, the intermediate slot having a width of less than twice the height of the substrate and advantageously in the range of 800 µm.

According to yet another characteristic of the microwave sensor according to the invention, the at least two connected transmission lines have a width of less than the height of the substrate and advantageously in the range of 100 µm.

According to yet another characteristic of the microwave sensor according to the invention, the at least two connected transmission lines are substantially of the same length of between 500 µm and 50 cm, and advantageously in the range of 47 mm.

The inventions further relates to the application of the microstrip microwave sensor to the characterization of liquid or solid samples.

A first advantage of the sensor according to the invention lies in the reliability in detecting the characteristics of the analysed materials.

Yet another advantage of the sensor according to the invention lies in its extreme simplicity of use and in that it avoids the destruction, modification or adaptation of the sample being analysed.

Yet another advantage of the sensor according to the invention lies in its very low cost and implementation.

Yet another advantage of the sensor according to the invention lies in its use in a gaseous, liquid or solid environment.

Yet another advantage of the sensor according to the invention lies in the repeatability and reliability of the result obtained by the measurement of the resonance frequency.

Yet another advantage of the sensor according to the invention lies in the extreme ease of use in that the sensor is fully or partially immersed in a liquid medium.

Yet another advantage of the sensor according to the invention lies in the reuse of the sensor by having a recyclable recipient of dimensions that are less than or equal to the dimensions of the sensor (at the length of the two lines) affixed to the connected transmission lines of the detector, fully or partially, and whose properties are well known and taken into account before the measurement of said material to be characterised.

Yet another advantage of the sensor according to the invention lies in the extreme ease of use of a microfluidic capillary device (microfluidic chamber or tube) arranged between the two connected transmission lines of the detector and whose properties are well known and taken into account before the measurement of the very small quantities of material.

BRIEF DESCRIPTION OF THE DRAWINGS

Other characteristics, particulars and advantages of the invention will be more apparent from the additional description given hereafter of the different embodiments given with reference to the appended drawings in which.

DETAILED DESCRIPTION OF THE EMBODIMENTS OF THE INVENTION

The invention will now be described in greater detail.

The sensor according to the invention has an architecture that resonates at a so-called resonance frequency that corresponds to the destructive interference between a transmitted wave and a reflected wave. This sensor is composed of a main transmission line that connects two ports (one input port and one output port, both being reversible) and at least two connected transmission lines. Resonance occurs when the direct wave propagating on the main line recombines in anti-phase with the wave reflected from the end of the two connected transmission lines. This recombination in anti-phase is known by the term "destructive interference" which is characterised by a peak in absorbance. This destructive interference occurs at the frequency verifying this anti-phase condition, this specific frequency being termed "resonance frequency".

Technologically, the sensor according to the invention is based on the implementation of microstrip technology. Furthermore, the present invention can also be applied to other technologies such as "stipline" or coplanar technology. According to these different technologies, the lines and the supporting ground plane are located in different or identical planes.

The rest of the description will refer to the implementation of a structure with two connected transmission lines, but it goes without saying that the number of lines may be greater than this, for example three or four lines, without the need for substantial modification of the structure.

Figure 1:
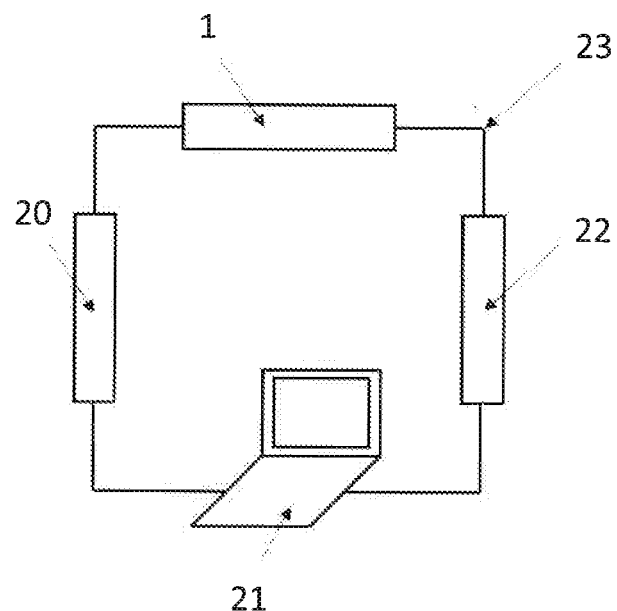
FIG. 1 shows an electrical circuit in which the sensor according to the invention may be integrated.

FIG. 1 shows an electrical circuit 23 for the implementation of the sensor 1 according to the invention, a frequency generator 20 producing sinusoidal signals, an acquisition system 21 for the signal envelope measurements performed, and an envelope detector 22. The frequency generator 20, the system 21 and the envelope detector 22 are commercially available products known in their function and further description does not need to be given.

Figure 2A:
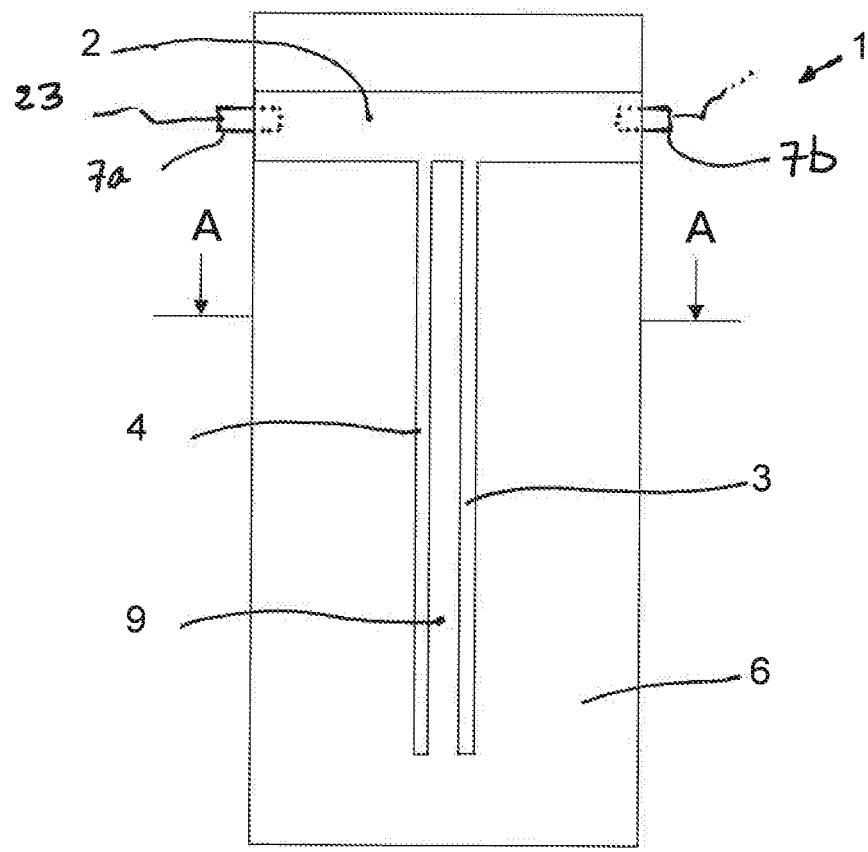
FIG. 2a shows a top view of the sensor according to the invention and FIG. 2b shows a section view along AA in FIG. 2a, FIG. 3a shows a solid sample being affixed to the detector in the slot.
Figure 2B:
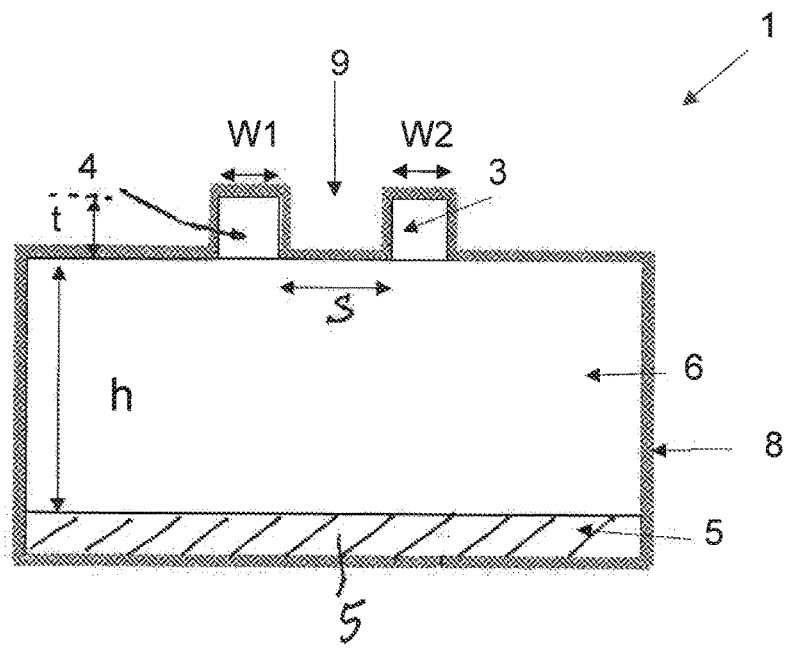

FIGS. 2a and 2b show the microwave sensor 1 according to the invention which is of the microstrip-type constituted by a main line 2 connected to the electrical circuit 23 in FIG. 1 by means of connectors or ports 7a and 7b and two connected transmission lines 3 and 4 integral at one extremity of the main line 2 and free at the other extremity. This sensor 1 is appropriate for measuring the dielectric properties of a solid or liquid material as will be explained hereafter. The main line 2 and the two connected transmission lines 3, 4 are made integral with a substrate 6. The two connected transmission lines 3, 4 are spaced from one another by a slot 9. This substrate may be, for example, Teflon or epoxy resin.

Lines 2, 3, 4 may be electrically conductive metallic materials such as, for example, copper or gold. They form one of the sensor's electrodes, the other electrode being constituted by the metallic support 5 on which the substrate is positioned or fixed.

Advantageously, the slot 9 is of a width in the range of 800 μm and each of connected transmission lines 3, 4 has a width of 100 μm and a length of 47 mm.

It goes without saying that the sensor according to the invention may comprise more than two connected transmission lines, for example three lines arranged identically with respect to one another.

The substrate 6 may be of a height or thickness (h) in the range of 800 μm with a permittivity of 2.55. According to the thickness selected according to the required configuration, this substrate 6 may be flexible, and thus of a thickness enabling deformation, or else rigid and thus not easily deformable.

According to the invention, the main line 2 has a width (1) giving it a characteristic impedance fixed in the range of 50 Ohm. The two connected transmission lines 3 and 4 are substantially of the same width and of a length equal to at least one quarter of the wavelength guided in the substrate 6 that corresponds to the resonance frequency of the sensor 1 in the air without the sample. The substrate 6 is of a height of between 500 and 5000 μm.

The main transmission line 2 has a characteristic impedance (Zc) preferably equal to 50 Ohm. Advantageously, the two adjacent and parallel transmission lines 3 and 4 are perpendicular to the main line 2. These two lines are of a length equal to one quarter of the length of the guided wavelength ($\lambda/4$), such wavelength corresponding to the initial working resonance frequency ($f_r$), frequency for which we wish to obtain the no-load resonance of the sensor, that is to say without the sample to be tested placed on the device.

These quarter-wave transmission lines 3 and 4 are open circuit (OC) corresponding to the microstrip terminology of "stubs" commonly used in this field. In this way, an impedance equivalent to a short circuit for a frequency equal to the resonance frequency is brought back into the impedance plane of the main line 2.

Lines 2, 3 and 4 are in the form of strips (or stubs).

The strips (or stubs) may be formed of transmission lines of a length L equal to the half-length of the guided wavelength ($\lambda/2$) on condition that they end at a short circuit (CC). In this way, an impedance equivalent to a short circuit for a frequency equal to the resonance frequency is brought back into the impedance plane of the main line 2.

Furthermore, the present invention in terms of performance and the wide range of targeted applications is based on a configuration corresponding to two lines $\lambda/4$ with slots (S) ending at an open circuit (CO).

Note that the input impedance of a line $\lambda/4$ ending in an open short-circuit is identical to the input impedance of a line $\lambda/2$ closed by short-circuit.

Line $\lambda/4$ in open circuit is optimal since it facilitates the small dimensions of the sensor according to the invention, the sensor's miniaturization and low cost. From a technological perspective, micro-production is less complex and quicker. Moreover, a line $\lambda/4$ is half the length of a line $\lambda/2$ closed in short circuit and does not require the substrate to be perforated to create the connection with the support 5 forming the ground plane.

FIG. 2b representing a transversal section along AA in FIG. 2a shows an insulating coating 8 constituted by a polymer enabling the assembly constituted by the substrate 6 and lines 2, 3 and 4 to be electrically insulated.

This insulating coating 8 is in the form of an envelope, closed except at the ports, where electrical access is needed for the input and output ports. It ensures the mechanical protection of the sensor and acts as an interface between the sensor 1 and the materials whose analysis is to be performed.

The insulating coating 8 is advantageously constituted by a layer of parylene with a thickness in the range of 1 to 5 μm. This polymer constitutes a dielectric coating and is inert with regard to most liquids. It insulates the whole of the device to ensure the sensor according to the invention is able to function in a liquid medium. Moreover, this polymer constitutes a hermetic, impermeable, form-fitting and biocompatible barrier with the other components of the sensor. The thickness of this polymer must, however, guarantee an optimal resonance of the present invention.

In other words, the insulating coating 8 has no substantial impact on the electromagnetic behaviour of the device and thus on its performances.

The characteristic impedance of stubs 3 and 4 may be equal to 50 Ohm, but different values may be adopted within the scope of the invention that are either lower or higher than this value according to the planned application and to the sample being studied.

The two stubs 3 and 4 are of widths W1 and W2 and preferably, W1=W2=W. Advantageously, the width W of stubs 3 and 4 is less than the height of the substrate. They are spaced by a distance d1 and d2 from the end of the substrate 6 and are separated by the slot 9 of width (s). The total length ($L_t$) of the main line 2 is equal to: $L_t$=d1+W1+S+W2+d2.

Preferably, d1=d2 is selected, but the functioning of the sensor according to the invention remains valid if this condition is not verified.

When a solid or liquid material is to be studied, it is placed in the slot 9 delimited by the two connected transmission lines 3, 4, said slot constituting reception means for said material to be analysed. If this is a liquid material, a recipient may be used or a sample of this liquid may be deposited directly on the sensor, and if it is a solid material, this may be applied directly onto the sensor.

The operating principle of the sensor according to the present invention is based on the coupling between the two stubs 3 and 4. This coupling defined by the slot 9 is essentially capacitive in nature and may be modelled by a capacitance between the two strips as a first approximation. This coupling is modified when a liquid or solid material under test (MUT) for which the relative permittivity is different from 1 ($\varepsilon r_{MUT} \neq 1$) is applied to the sensor or in the slot for a material of small quantity or dimensions.

Thereafter, a material is considered of a width Wmut=s, a height h2 advantageously in the range of that of the substrate (h2=1 mm; or h2≈h) and the same length $L_{stub}$ as the two stubs 3 and 4. This material MUT has a relative permittivity of $\varepsilon r_{MUT} = \varepsilon_{r2}$ (a priori unknown) whereas the permittivity of the substrate 6 of the sensor is well known ($\varepsilon_{r1}$=2.55).

Figure 3A:
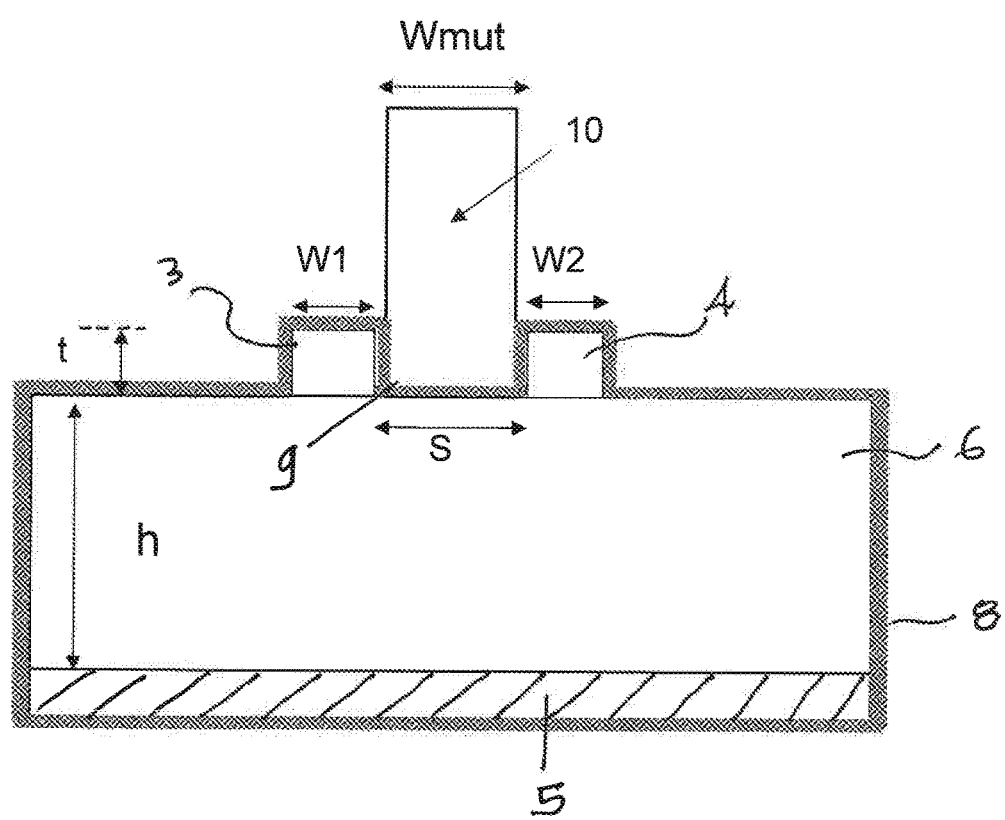
FIG. 3b shows a solid sample being applied to the lines of the detector.
FIG. 3c shows a sold sample being affixed to the whole surface of the detector.
FIG. 3d shows a recipient containing a sample in the slot in the detector.
FIG. 3e shows a tube being affixed in the slot in the detector.

FIG. 3a represents a material MUT 10 to be tested affixed to the sensor 1 previously described. In this configuration, the material 10 is inserted between the two stubs 3 and 4.

With regard to the ground plane, the stubs 3 and 4 constitute two open circuit capacitances (Co). This capacitance Co is expressed by the relation:

$$Co = \varepsilon o \cdot \varepsilon r_{eff\_A} \cdot (L_{stub} \cdot S)/h$$

in which $\varepsilon r_{eff\_A}$ corresponds to an effective relative permittivity of the electromagnetic environment between stubs 3 and 4, normally impacted by $\varepsilon_{r1}$, $\varepsilon_{r2}$, h, S and $W_{MUT}$, $L_{stub}$ the length of the stubs, S the width of the slot and h the height of the substrate.

Similarly, the coupling capacity $C_1$ between stubs 3 and 4 may be expressed by the relation:

$$C_1 = \varepsilon o \cdot \varepsilon r_{eff\_B} \cdot (L_{stub} \cdot S)/t$$

in which $\varepsilon r_{eff\_B}$ corresponds to an effective relative permittivity of the electromagnetic environment located between stubs 3 and 4, normally impacted by $\varepsilon_{r1}$, $\varepsilon_{r2}$, t, S et $W_{MUT}$, $L_{stub}$ the length of the stubs, S the width of the slot and t the thickness of the stubs.

$$\varepsilon r_{\mathit{eff\_B}} = f(\varepsilon_{r1}, \varepsilon_{r2})$$

The relative permittivity value $\varepsilon_{r1}$ of the material 8 essentially impacts the value of capacitance $C_1$ and consequently the resonance frequency of the structure.

In the invention, the capacitive coupling modelled by $C_1$ is preferred to capacitances $C_o$. To obtain this result, it is necessary for capacitance $C_1$ to be greater than $C_o$, which supposes the three following conditions be respected:

For $C_1 > C_o$:
1. W<<h: the width of stubs 3 and 4 must be much less than the height of the substrate 6,
2. S<2·h: the width of the slot 9 must be less than twice the height of the substrate 6,
3. Wmut≥S: the width of the material 10 must be at least equal to the width of the slot 9.

The height of the substrate 6 is of small dimensions (a few hundred micrometres), consequently, the device will have:
widths for the stubs 3 and 4 in the range of a hundred micrometres. However, this width W must be greater than the thickness of the metallization t (W>t), which is consistent with technological production constraint; a slot width S in the range of a few hundred micrometres to a few millimetres according to the height of the substrate considered.

These conditions are required to ensure capacitive coupling and enable the modelling presented hereafter.

Figure 3B:
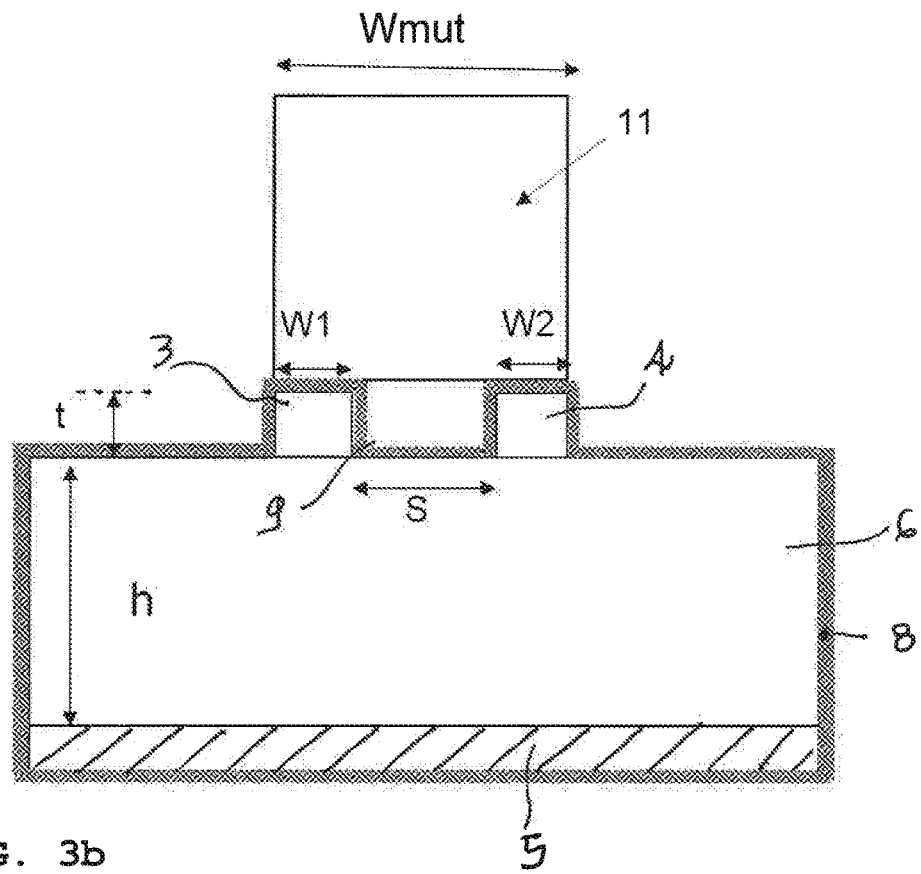

FIG. 3b shows the sensor from FIG. 3a but using a material 11 whose width is equal to the sum of the widths of stubs 3 and 4 and slot 9, the other elements remaining unchanged.

Figure 3C:
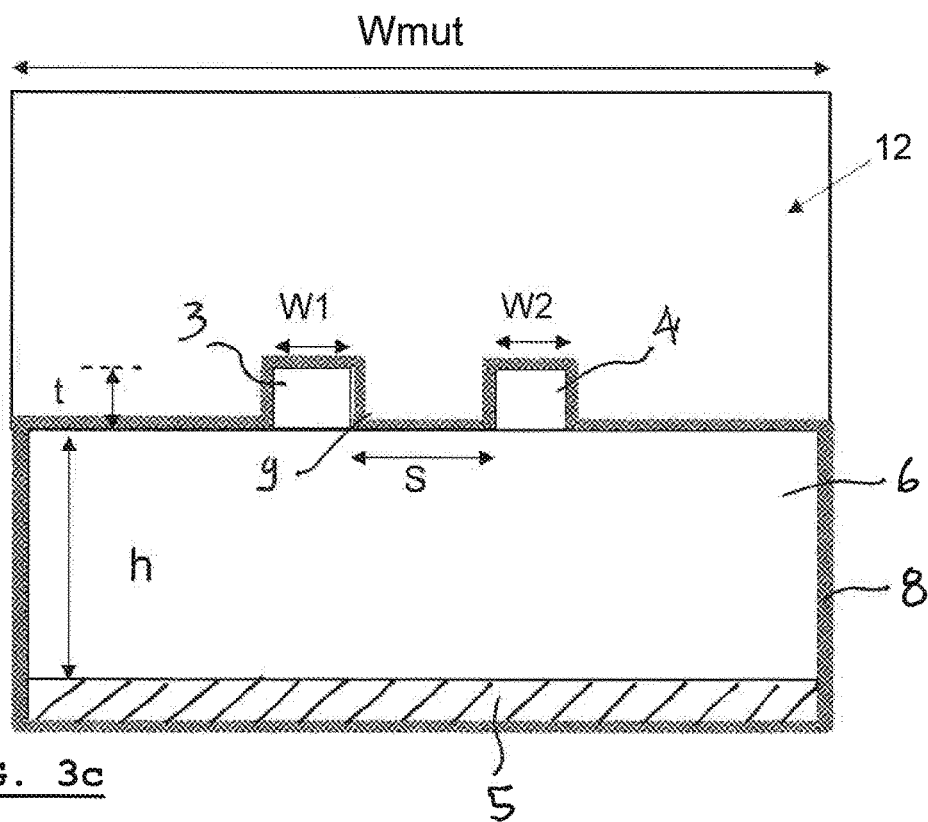

FIG. 3c shows the sensor from FIG. 3a but using a material 12 whose width is equal to that of the substrate 6, the other elements remaining unchanged.

It is understood that in the case of configurations 3b and 3c, the previously described conditions are respected.

Figure 3D:
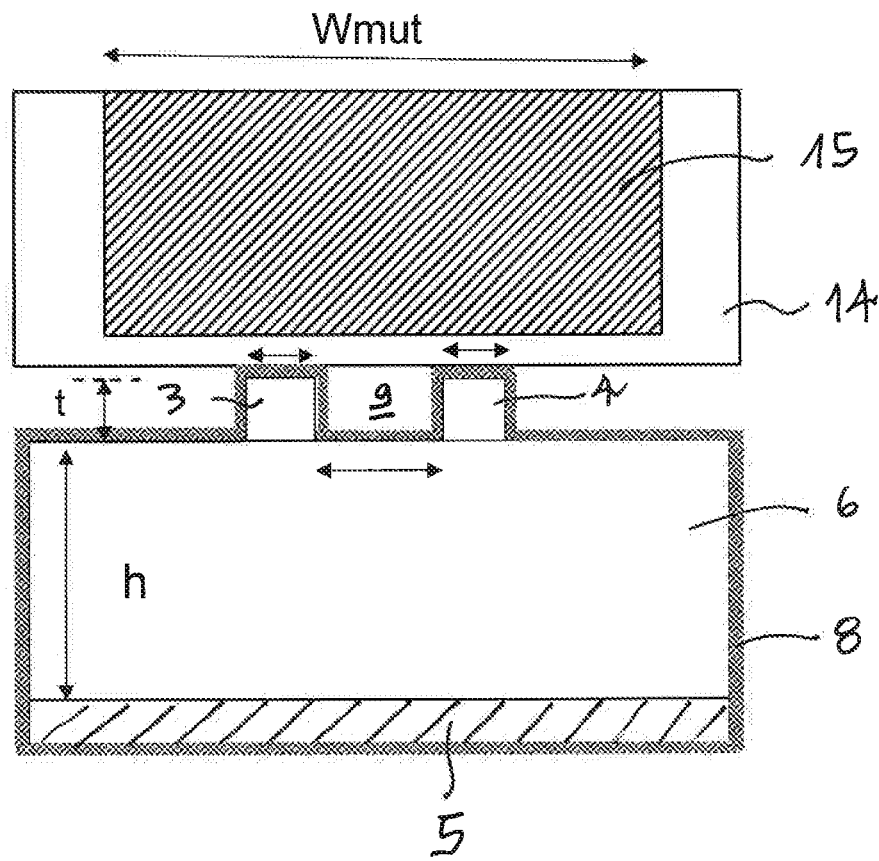
Figure 3E:
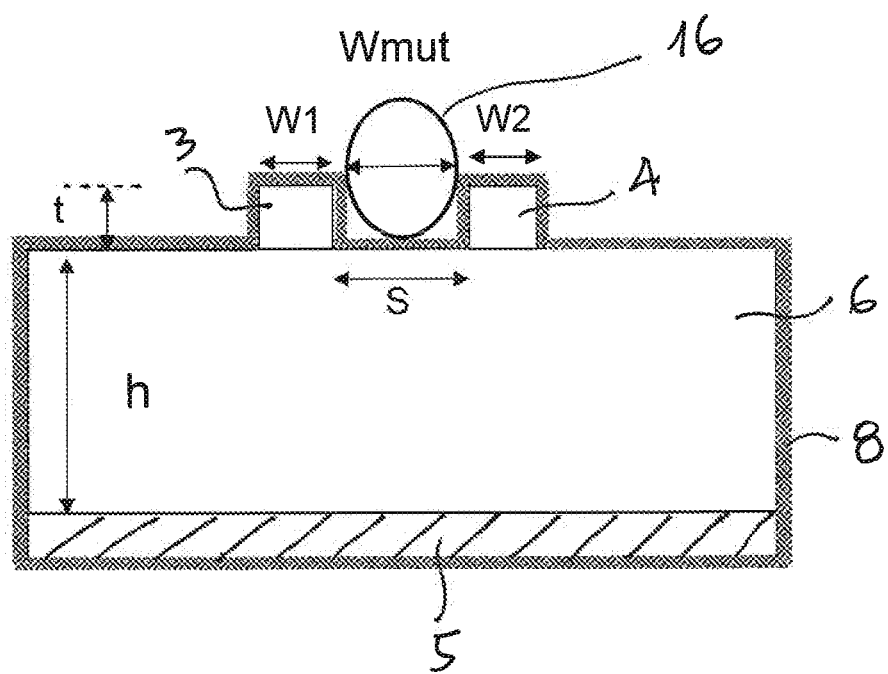

FIG. 3d shows a receptacle 14 positioned on lines 3 and 4 of the detector. It goes without saying that the constitutive material of this receptacle may have a permittivity of 2.55 and be made of Teflon or epoxy resin. It may be used for powdery material or for liquids.

FIG. 3d shows a fluid duct 16 arranged in the slot 9 enabling a liquid to be analysed to circulate between the stubs. This duct 16 may be in the form of a tube or trough. It goes without saying that the constitutive material of this duct 16 may have a permittivity of 2.55 and be made of Teflon or epoxy resin.

Figure 4A:
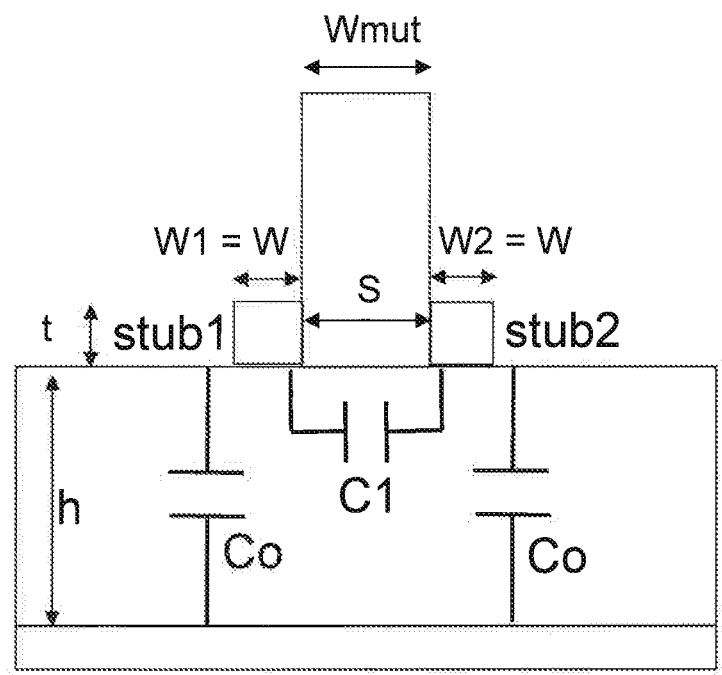
FIGS. 4a and 4b show the operating principle of the sensor according to the invention from an electrical and dimensional point of view.
Figure 4B:
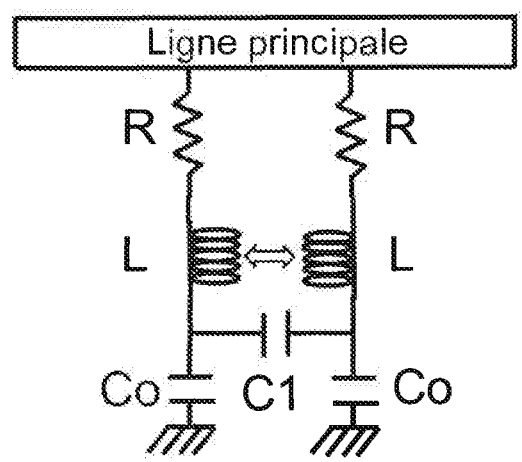

FIGS. 4a and 4b show a sensor 1 according to the invention according to an LRC equivalent circuit diagram in function of capacitances $C_0$ and $C_1$. The capacitive coupling is namely introduced into this representation by means of capacitance $C_1$.

Also, it is considered that inductances L constituent a mutual inductance so as to model the magnetic coupling between the strips or stubs, this magnetic coupling is negligible, however, compared to the electrical coupling (capacitive).

The equivalent circuit diagram of the whole device is detailed in FIG. 4b. This equivalent circuit diagram includes that of the R-L-C type stub involving the capacitance $C_o$ for each of them.

The equivalent circuit diagram for FIG. 4b does not involve the notion of line elements and line sections as found in the literature, especially in line theory.

Figure 5A:
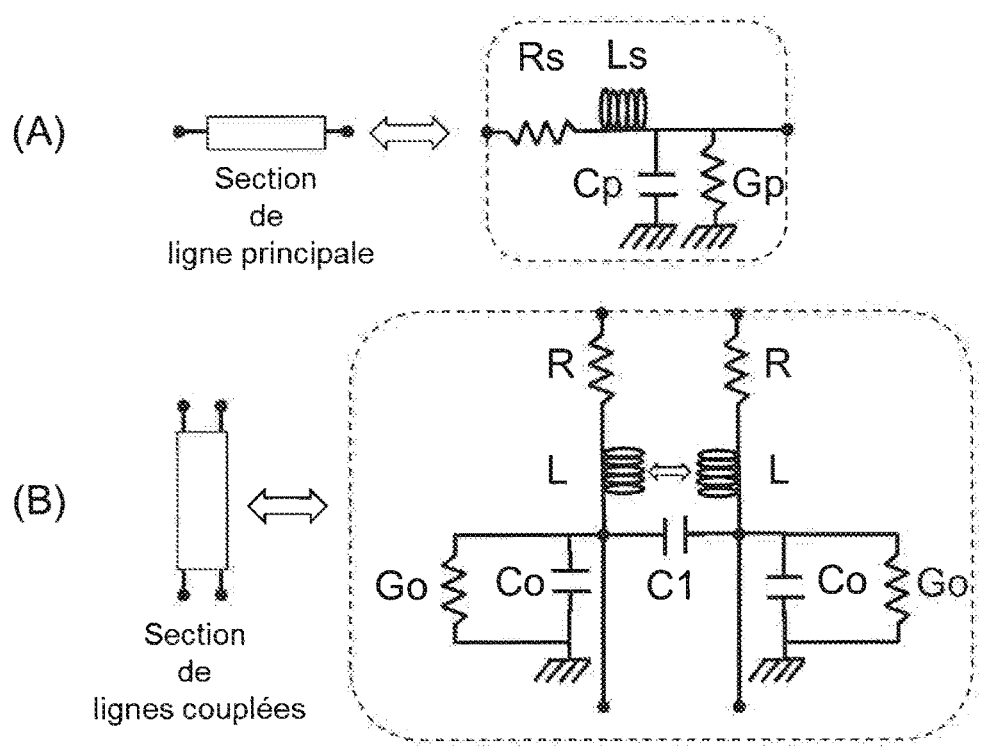
FIG. 5a shows the description of the sections of the main line and the two connected transmission lines, FIG. 5b show the description of the electrical circuit diagram equivalent to the sensor according to the invention and corresponding to the global description of the sections in FIG. 5a, FIG. 6a shows the frequency evolution of the transmission parameter noted $S_{21}$ of the sensor according to the invention for different types of materials under testing listed by the value of their relative permittivity.
Figure 5B:
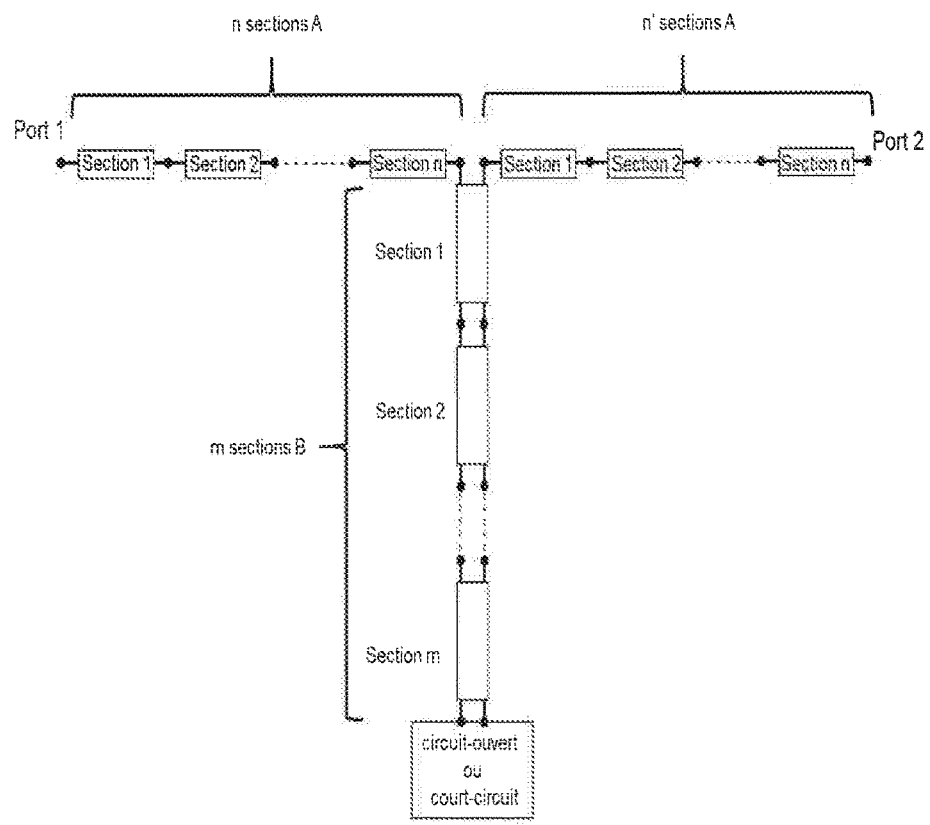

FIGS. 5a and 5b show an equivalent electrical circuit diagram that adopts a representation involving these concepts. For this, models of the type R-L-C-G of the main transmission line (A) section and the coupled lines (B) section are introduced, where:

Rs, Ls, Cp, Gp respectively correspond to the resistances, inductances, capacitances and linear conductance of a length or section of the main transmission line. Preferably, these elements are dimensioned to obtain a characteristic impedance equal to 50 Ohm with the lowest possible linear losses. The distances d and d' (parts of the main transmission line located on either side of the coupled stubs) may be different, the number of sections adopted is also different for each of them (n and n')

R and Go represent the linear resistance and the parallel conductance (parasitic) of the coupled lines. The linear inductance L is a mutual linear inductance (magnetic coupling) between the lines. The capacitance Co here is a linear capacitance of each line (stub) and C1 models the linear capacitive coupling.

The equivalent circuit diagram shown in FIG. 4b is a simplification to show the interest of the invention but is a symbolic representation whereas FIGS. 5a and 5b show a strict equivalent electrical circuit diagram from a technical perspective based on the transmission line theory.

With regard to the performance of the sensor and in cases where the operational conditions are verified, the electrical field lines are confined near to the surface of the substrate 6 between the two stubs 3 and 4. Consequently, the presence of a material modifies this confinement (disturbance of the electromagnetic environment) and its permittivity impacts the resonance frequency with what can be very high sensitivity. The sensitivity is defined as the variation in the resonance frequency ($\Delta f = f_{r1} - f_{r2}$) observed when the permittivity of the material MUT is modified (variation of permittivity $\Delta\varepsilon_r$ and thus variation of the capacitance C1).

As shown by the detailed measurements presented hereafter, the sensitivity of the sensor according to the invention is very high, which is a great advantage when differentiating two materials of close permittivity.

A further advantage of the sensor according to the invention lies in the use of direct capacitive coupling between the two connected transmission lines (capacitance C1 of the equivalent circuit diagram) and capacitive coupling between each of these lines and the ground plane (capacitances Co of the equivalent circuit diagram) providing increased sensitivity and thereby enabling high measurement accuracy for large or small quantities of material to be characterised.

Figure 6A:
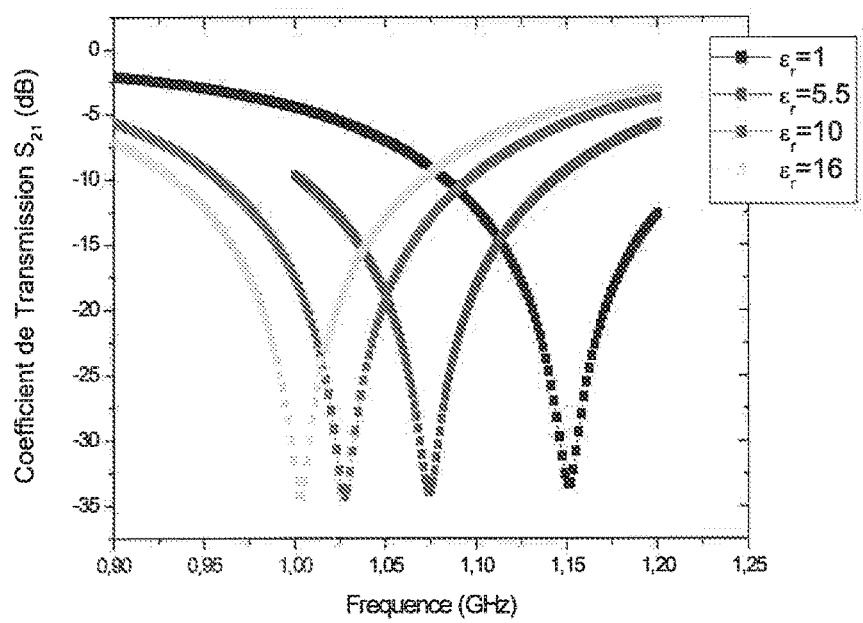
FIG. 6b shows the evolution of the resonance frequency of as a function of the relative permittivity $\varepsilon_r$ of the sample.
Figure 6B:
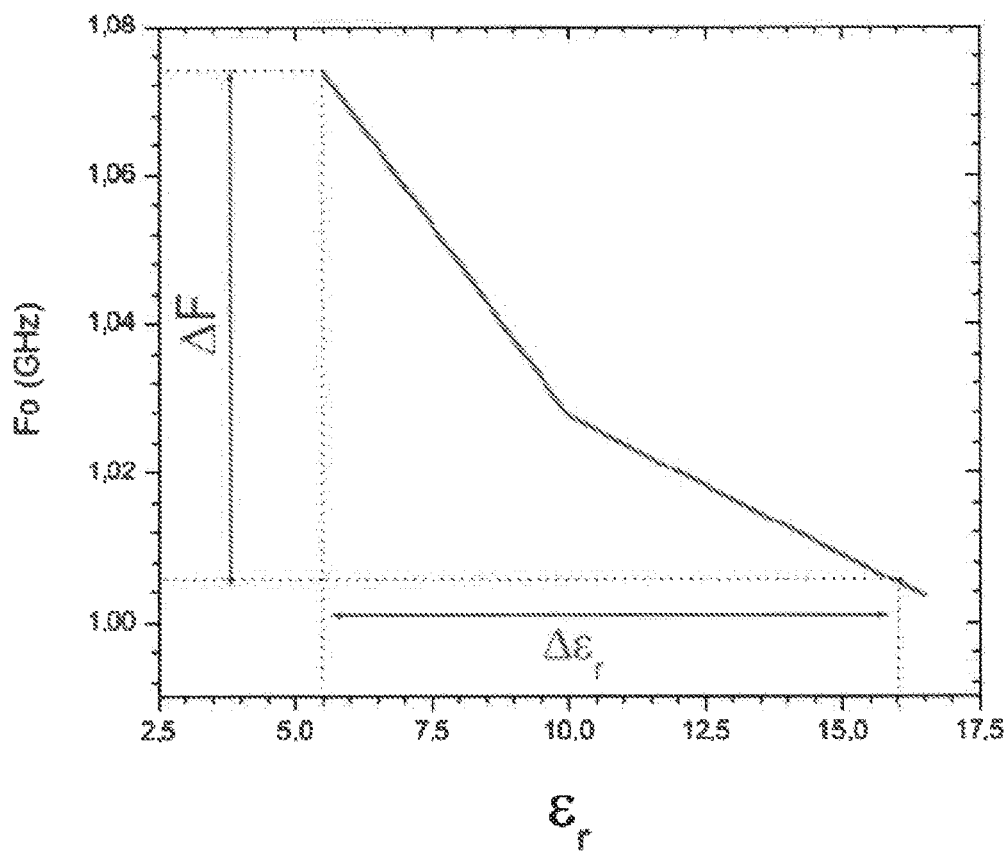
Figure 7:
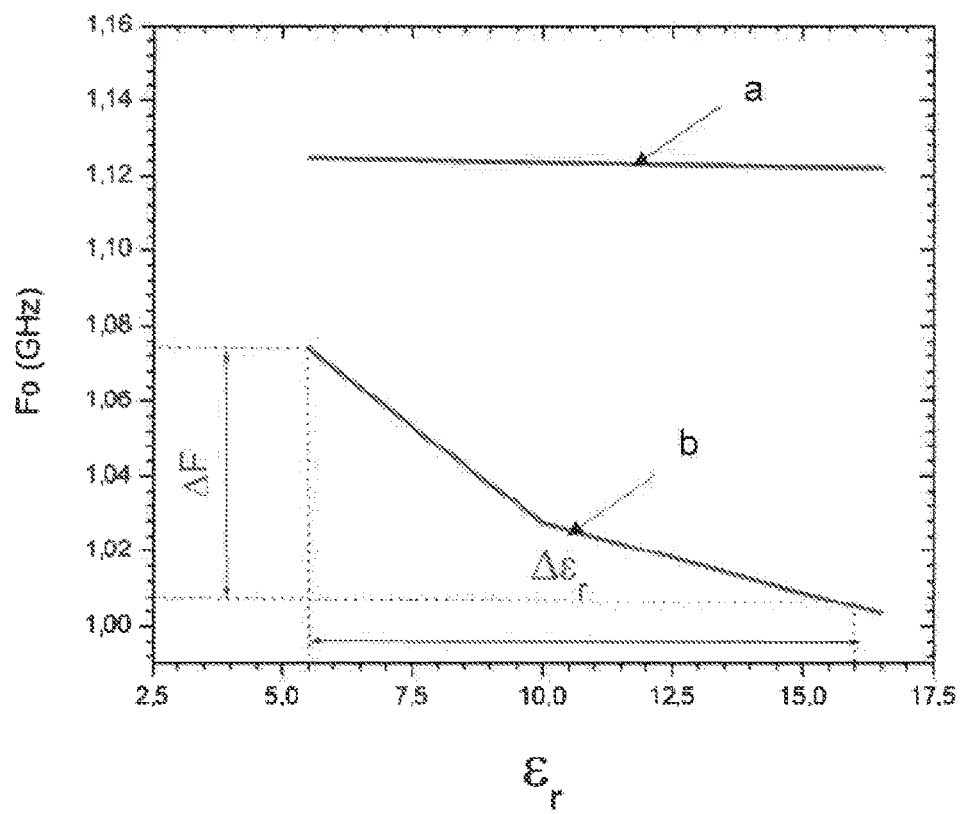
FIG. 7 shows the frequency evolution of the transmission coefficient $S_{21}$ for two slot width values compared to the width of the sample.
Figure 8:
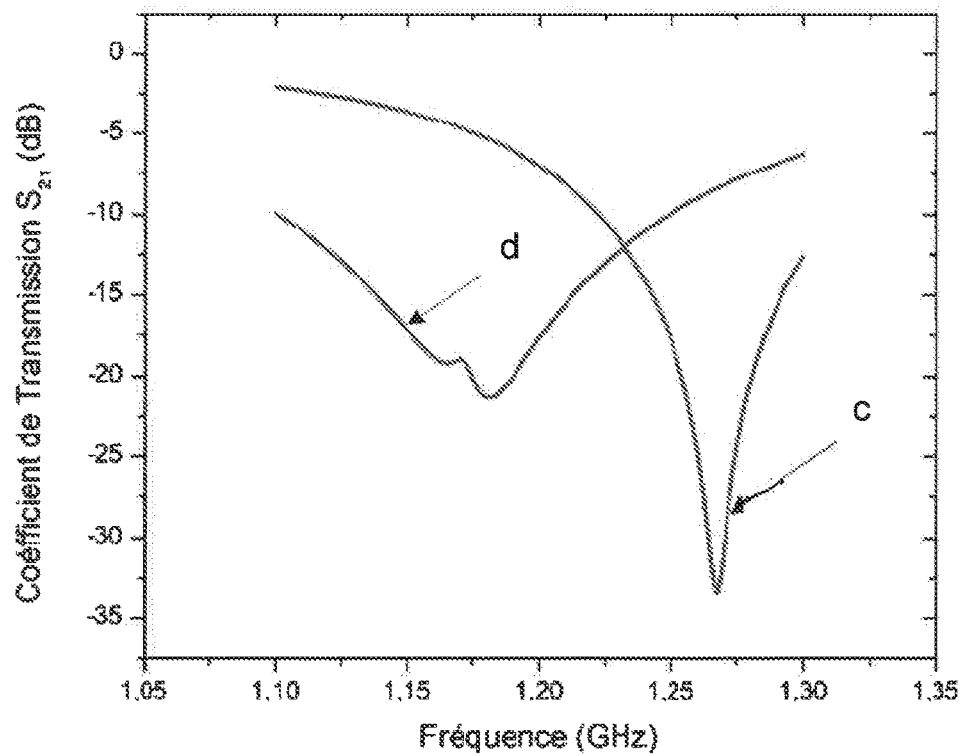
FIG. 8 shows the frequency evolution of the transmission coefficient $S_{21}$ for two slot width values compared to twice the substrate height.

In the specific examples given in relation to FIGS. 6-8, a slot 9 is selected with a width S=800 μm. This is equal to the width of the material MUT to be tested, that is 800 μm. The width of stubs 3 and 4 is equal to W1=W2=W=100 μm.

The length of stubs 3 and 4 is selected so as to have a no-load resonance frequency greater than 1 GHz.

($L_{stub}$=47 mm for a frequency fr=1.15 GHz)

Since h=800 μm, this configuration fully corresponds to the two conditions $$W<<h \text{ and } S<2*h.$$

FIGS. 6a and 6b show the frequency response of the sensor according to the invention for different materials tested. The frequency response of the sensor may be characterised by its transfer function H(f) or by the diffusion parameter from the input of the sensor to its output as a function of frequency. This parameter is generally noted s21 which represents the transmission coefficient of the measurement signal and the resonance frequency evolution for different materials of different natures respectively the evolution of parameter s21 and the evolution of the resonance frequency of the material under test (MUT).

FIG. 6a shows the evolution of the transmission coefficient $S_{21}$ as a function of frequency, of which the modulus is determined by numerical electromagnetic simulation in three dimensions (HFSS simulation tool) for different permittivity values attributed to the MUT.

These materials are glass (εr=5.5), sapphire (εr=10) and diamond (εr=16). Case εr=1 is air, the sensor having no material in this case.

These materials thus deliver a frequency response that is characteristic of their nature and may be clearly differentiated.

FIG. 6b shows the variation in the resonance frequency for different values of the relative permittivity ε of the material MUT. It can be seen that for a variation in permittivity $\Delta\varepsilon_r$=10, the variation in resonance frequency (Δf) is greater than 70 MHz.

Note that the instrumentation associated with the device (preferably a vector network analyser) easily enables frequency variations Δf of less than 1 kHz to be differentiated. Very low variations in permittivity may therefore be detected using the device according to the invention thus enabling any type of material to be accurately characterised.

When the width of the material to be tested is less than that of the slot 9, the capacitive coupling is clearly altered or even inexistent. The electric field then hardly penetrates the material.

Because of this, the device's sensitivity is greatly reduced. This type of configuration should therefore be avoided.

FIG. 7 shows the variation in resonance as a function of frequency in the case of a difference in width between the slot 9 and the sample of material 10.

The curve (a) illustrates the case where the width of the sample is less than the width of the slot and curve (b) the case where the width of the sample is the same as that of the slot. It can be observed that the sensitivity, which is of 70 MHz is case S=Wmut (curve b) plunges to 2.7 MHz when S=1 mm and Wmut=800 μm (curve a).

On the other hand, it is perfectly possible for the material to be wider than the slot since in this case the sensitivity is improved. From an application perspective, the slot 9 shall be dimensioned so that it is always of smaller width than the material to be tested.

The case has also been studied where the width of the slot is much greater than the height of the substrate 6. For a microstrip line, the electric field is confined between one of stubs 3 and 4 and the support 5. The fact of reducing or increasing the space between the two stubs modifies this distribution. If the two stubs 3 and 4 are sufficiently close to one another with respect to the height of the substrate (s<2·h) the electric field will be confined between these two stubs.

FIG. 8 illustrates the evolution of the transmission coefficient s21 as a function of the frequency for two width values of the slot. Curve (c) represents the case where the width of the slot is less than twice the height of the substrate and curve (d) the case where the width of the slot is more than twice the height of the substrate.

When the slot width is too wide with respect to the height of the substrate, the quality of the resonance is severely affected. Thus, curve (c) illustrates the evolution of parameter S21 as a function of the frequency in the case where the condition S<2*h is verified and curve (d) the opposite case where S>2*h. This comparison demonstrates that the resonance quality is altered by a lower quality factor Q=Δf/fr, such as to compromise the targeted application.

In the case where S>2*h a highly degraded frequency selectivity can be observed since the resonance is not as deep, and there is a spreading of the resonance in the frequency range.

So as to demonstrate the full advantages of the invention, the inventors have reproduced the architecture proposed in the Muhammad Amin et al document previously analysed as hereafter designated as the reference.

Figure 9:
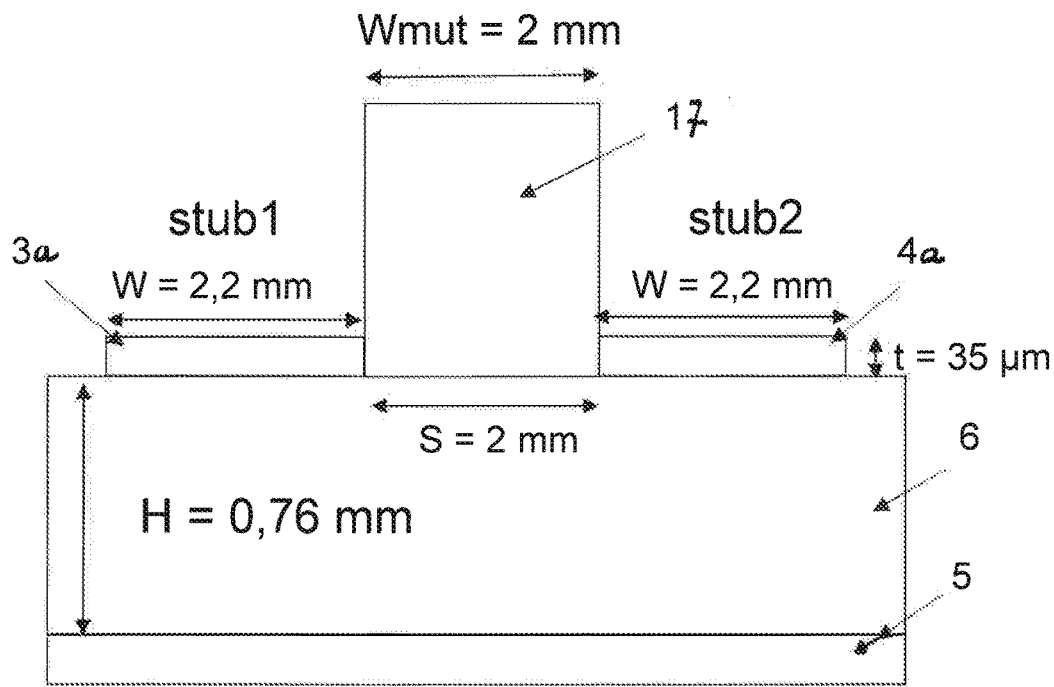
FIG. 9 shows a reference of prior art.

The reference is reproduced in FIG. 9 and the transversal dimensions disclosed for the sensor according to the invention are used, namely the substrate 6 has a height of 0.76 mm, the slot a width of 2 mm in which the material 17 is inserted, the two stubs 3 and 4 on either side of the slot have a width of 2.2 mm and a metallic layer 5 is of a thickness of 35 μm.

It is furthermore noted that the conditions W<<h and S<2·h are not verified for the reference case. The length of the stubs used in the invention is retained, knowing that this only defines the possible no-load resonance frequency. Additionally, a material is considered that has a width the same as that of the slot (Wmut=S) in order to compare and contrast the two architectures in equivalent conditions of use.

Figure 10:
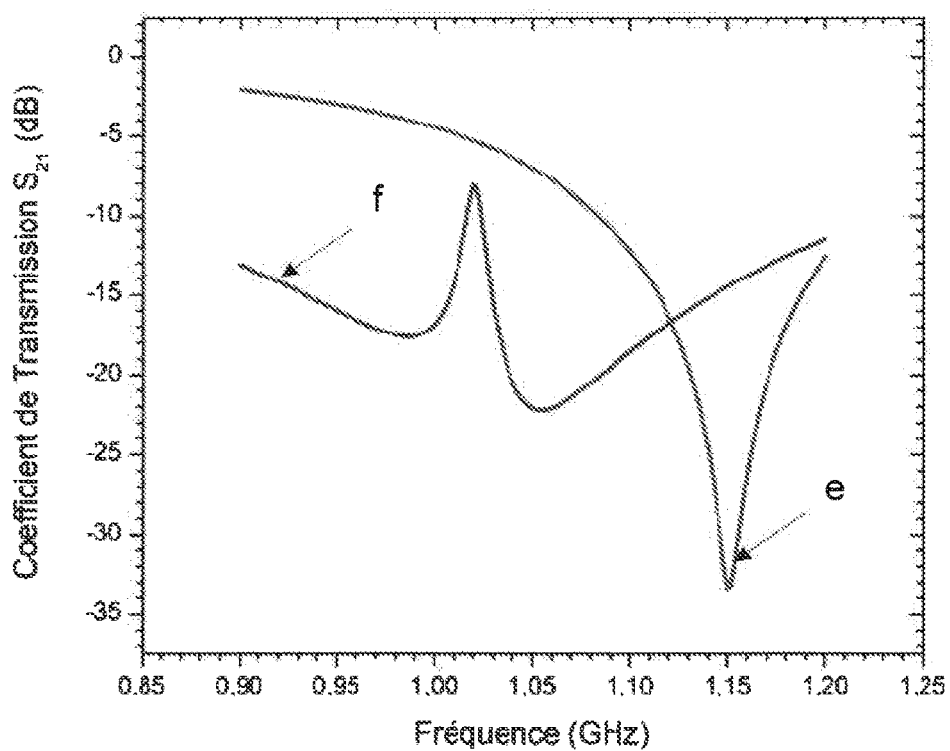
FIG. 10 shows the evolution of the transmission coefficient $S_{21}$ as a function of the frequency for the reference and for the sensor according to the invention.

FIG. 10 shows the frequency evolution for the transmission coefficient S21 of the sensor according to the invention (curve e) and the transmission coefficient S21 of the device according to the reference case (curve f) for the same material under test.

The electromagnetic behaviours can be seen to be very different: in the case of the sensor according to the invention, the frequency evolution of the transmission coefficient (curve e) highlights a resonance frequency associated with destructive interference. For the reference case device, the frequency evolution of the transmission coefficient S21 (curve f) is totally different with no resonance frequency associated with destructive interference.

Furthermore, after analysis of the distribution of the electric field, an absence of capacitive coupling can be noted for the reference case. The capacitance C1 modelling the capacitive coupling and previously described therefore does not occur in the equivalent electrical diagram for the reference device. This capacitance, furthermore, is neither mentioned nor introduced into the equivalent electrical diagram by the authors of the reference.

The equivalent electrical diagram and the operating electrical diagram are therefore very different for the reference case and for the sensor according to the invention.

Figure 11:
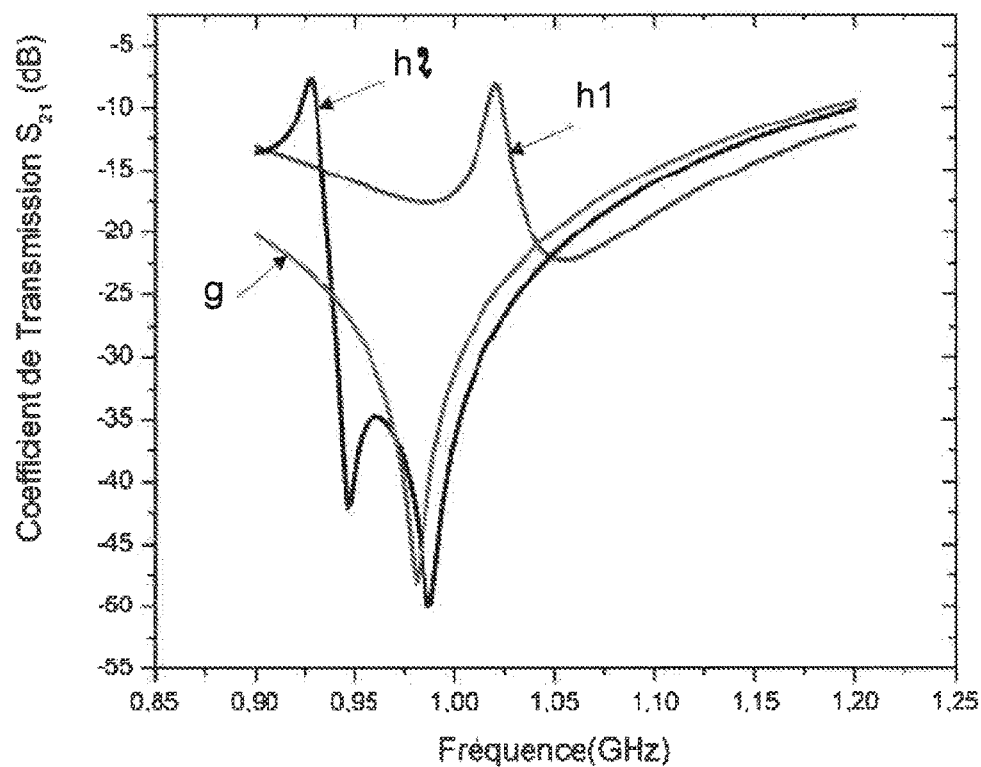
FIG. 11 shows the frequency evolution of the transmission coefficients $S_{21}$ for three samples examined by the reference.

FIG. 11 show the frequency evolution of the transmission coefficient S21 for the reference in FIG. 9 for three permittivity values. The frequency evolution of the transmission coefficient S21 can be seen to be totally different for the three materials tested with different permittivities (curves h1, h2 and g) for the reference in FIG. 9. Curve h1 does not show resonance linked to destructive interference whereas curve h2 shows two resonances linked to destructive interference and curve g shows a single resonance of this type.

The reference architecture therefore does not enable a correlation to be made between a resonance frequency and a permittivity value. As a result, the reference may in no way be used as a sensor.

The increase in frequency of the sensor according to the invention requires the length $L_{stub}$ of the stubs to be reduced. The ultimate limit to this reduction is the aspect ratio, which must be $L_{stub}/W$>5. In the case of the conventional use of stubs, their characteristic impedance is of 50 Ohm, which corresponds to a width of W=2.2 mm considering the substrate in the previously presented example in FIGS. 6a and 6b ($\varepsilon_r$=2.55, h=800 μm).

In the case of the sensor according to the invention, it is recalled that the condition W<<h implies that W be in the range of a hundred micrometres.

However, the theory imposes L=$\lambda$g/4=$\lambda$o/(4·$\varepsilon_r^{1/2}$) where:
$\varepsilon_r$ is the permittivity of the substrate ($\varepsilon_r$=2.55) in our example,
$\lambda$g is the guided wavelength,
$\lambda$o is the wavelength in vacuum: $\lambda$o=c/f,
f is the frequency.

The maximal operating frequency of the stub may be defined as equal to:

$$f\max = c/\lambda o = c/(L_{stub\text{-}min} \cdot (4 \cdot \varepsilon_r^{1/2})) \text{ with } L_{stub\text{-}min} = 5 \cdot W$$

That is fmax=c/(W·20·$\varepsilon_r^{1/2}$)

In the case of a sensor using only 50 Ohm microstrip lines (W=2.2 mm for $\varepsilon_r$=2.55 and h=800 μm), a minimal stub length is obtained $L_{stub\text{-}min}$=11 mm and consequently a maximal operating frequency of 4.3 GHz.

In the case of the sensor according to the invention, the connected transmission lines are of a width W=100 μm, which imposes a maximal length $L_{stub\text{-}min}$ in the range of 500 μm and thus a maximal frequency in the range of 94 GHz.

The sensor according to the invention thus has dimensions conducive to an increase in frequency.

It is then shown that this frequency increase is associated with a strong increase in sensitivity.

Figure 12:
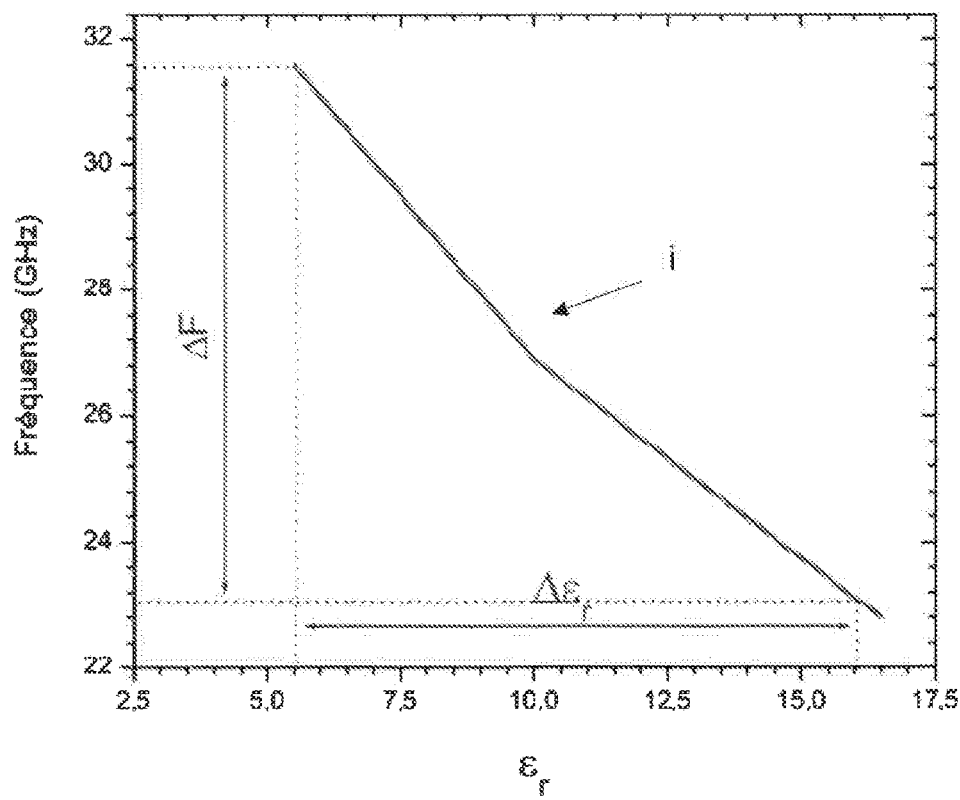
FIG. 12 shows the variation of the high-frequency resonance frequency as a function of the permittivity of the sample.

An example of a significant result is proposed in FIG. 12. The configuration studied for the sensor according to the invention corresponds to a stub width and length respectively of 100 μm and 4 mm.

In this Figure, the curve (i) represents the variation in resonance frequency as a function of permittivity.

A variation in the resonance frequency of 8.8 GHz can be noted for a relative permittivity varying from 5.5 (glass) to 16.5 (diamond). In the case of a stub length of 4 mm, the resonance frequency varies by 8.8 GHz between the test performed on a sample of glass and one performed on a sample of diamond.

By way of comparison, in the case of a stub length of 47 mm, the resonance frequency varies by 70 MHz between the test performed on a sample of glass and one performed on a sample of diamond.

The architecture of the sensor to which this invention relates may be modelled by an equivalent electrical diagram which, according to prior art, is unprecedented.

This equivalent electrical diagram results in capacitive coupling between stubs 3 and 4, coupling which, to be applied, imposes clearly identified conditions on the architecture dimensions.

Among these conditions, the very small width imposed for stubs 3 and 4 enables their length to be reduced, and in this way, enables an increase in frequency which offers a breakthrough combination of compactness and sensitivity of this device in its high frequency configuration.

As indicated previously, the sensor 1 according to the invention may be implemented to characterize the dielectric properties of small amounts, for example 0.001 mm³ or large quantities (several dm³) of solid or liquid materials at different frequencies.

The sensor 1 eliminates the need for complex set-ups and the destruction of the sample.

The sensor 1 according to the invention thus offers industry a great number of applications requiring strict protocols where the samples analysed are not reusable.

Frequency analysis, on which the sensor 1 according to the invention is based, enables simple non-destructive analysis of the sample.

The sensor according to the invention enables the differentiation of each frequency signature of characterized materials defined by their permittivity but also by their losses.

The invention claimed is:

1. A microstrip microwave sensor for a measurement of dielectric properties of a solid or liquid material, the microwave sensor comprising:
   a substrate;
   a metallic support;
   a main line;
   at least two connected transmission lines integral at one of their extremities to the main line, the main line and the at least two connected transmission lines being spaced from one another by a slot and being made integral with the substrate, wherein:
      the at least two connected transmission lines extends over an upper conductive surface of the substrate such that a height of the slot is greater than zero and forms a reception means for the solid or liquid material,
      the slot has a width of less than twice a height of the substrate,
      the main line is connected to an electrical circuit by each of its two respective extremities to inject a sinusoidal signal,
      said main line has a width giving it an impedance in a range of 50 Ohm,
      the at least two connected transmission lines are substantially of a same width, the width being less than the height of the substrate,
      the at least two connected transmission lines are of a length equal to at least one quarter of a wavelength guided in the substrate,
      the substrate has the height or a thickness giving it flexibility or rigidity, and
      the substrate is applied to the metallic support formed of a layer of metallic material.

2. The microstrip microwave sensor according to claim 1, wherein an assembly formed by the substrate, the main line and the at least two connected transmission lines is electrically insulated by means of an insulating coating formed of a thin layer of a polymer.

3. The microstrip microwave sensor according to claim 2, wherein the insulating coating is formed of parylene with a thickness in a range of 1 to 40 μm.

4. The microstrip microwave sensor according to claim 1, wherein the slot has a width in a range of 100 μm to 5 mm.

5. The microstrip microwave sensor according to claim 1, wherein the metallic support has a thickness in a range of 35 μm.

6. The microstrip microwave sensor according to claim 1, wherein the height of the substrate is of between 500 and 1500 μm.

7. The microstrip microwave sensor according to claim 1, wherein the substrate has a permittivity of between 1 and 40.

8. The microstrip microwave sensor according to claim 1, wherein the slot delimited by the at least two connected transmission lines forms the reception means for said solid or liquid material.

9. The microstrip microwave sensor according to claim 1, wherein the height of the substrate is of between 500 and 1500 μm.

10. The microstrip microwave sensor according to claim 1, wherein the at least two connected transmission lines is two connected transmission lines.

11. The microstrip microwave sensor according to claim 10, wherein the two connected transmission lines are substantially of a same length of between 500 μm and 50 cm.

* * * * *